United States Patent
Chopra et al.

(10) Patent No.: US 9,937,365 B2
(45) Date of Patent: Apr. 10, 2018

(54) DUAL ACTION DENTIFRICE COMPOSITIONS TO PREVENT HYPERSENSITIVITY AND PROMOTE REMINERALIZATION

(75) Inventors: Suman K. Chopra, Monroe, NJ (US);
Lynette Zaidel, Cranford, NJ (US);
Michael Prencipe, Princeton Junction, NJ (US)

(73) Assignee: Colgate-Palmolive Company, New York, NY (US)

( * ) Notice: Subject to any disclaimer, the term of this patent is extended or adjusted under 35 U.S.C. 154(b) by 675 days.

(21) Appl. No.: 13/262,010

(22) PCT Filed: Apr. 1, 2010

(86) PCT No.: PCT/US2010/029684
§ 371 (c)(1),
(2), (4) Date: Sep. 29, 2011

(87) PCT Pub. No.: WO2010/115039
PCT Pub. Date: Oct. 7, 2010

(65) Prior Publication Data
US 2012/0021031 A1   Jan. 26, 2012

Related U.S. Application Data

(60) Provisional application No. 61/165,749, filed on Apr. 1, 2009.

(51) Int. Cl.
| | |
|---|---|
| *A61K 8/25* | (2006.01) |
| *A61K 8/21* | (2006.01) |
| *A61Q 11/00* | (2006.01) |
| *A61K 8/02* | (2006.01) |
| *A61K 8/20* | (2006.01) |
| *A61K 8/19* | (2006.01) |

(52) U.S. Cl.
CPC ........... *A61Q 11/00* (2013.01); *A61K 8/19* (2013.01); *A61K 8/20* (2013.01); *A61K 8/25* (2013.01); *A61K 2800/412* (2013.01)

(58) Field of Classification Search
None
See application file for complete search history.

(56) References Cited

U.S. PATENT DOCUMENTS

| | | | |
|---|---|---|---|
| 3,574,824 A | 4/1971 | Kapadia | |
| 3,863,006 A | 1/1975 | Hodosh | |
| 4,631,185 A | 12/1986 | Kim | |
| 5,160,737 A | 11/1992 | Friedman et al. | |
| 5,330,746 A | 7/1994 | Friedman et al. | |
| 5,449,509 A * | 9/1995 | Jackson et al. | 424/49 |
| 5,670,137 A | 9/1997 | Ascione | |
| 5,735,942 A * | 4/1998 | Litkowski et al. | 106/35 |
| 5,834,008 A | 11/1998 | Greenspan et al. | |
| 5,843,409 A | 12/1998 | Campbell et al. | |
| 5,891,233 A | 4/1999 | Salonen et al. | |
| 5,972,384 A | 10/1999 | Thut et al. | |
| 5,977,204 A | 11/1999 | Boyan et al. | |
| 5,990,380 A | 11/1999 | Marotta et al. | |
| 6,086,374 A | 7/2000 | Litkowski et al. | |
| 6,096,292 A | 8/2000 | Halecky et al. | |
| 6,190,643 B1 | 2/2001 | Stoor et al. | |
| 6,244,871 B1 | 6/2001 | Litkowski et al. | |
| 6,306,925 B1 | 10/2001 | Clupper et al. | |
| 6,338,751 B1 | 1/2002 | Litkowski et al. | |
| 6,342,207 B1 | 1/2002 | Stoor et al. | |
| 6,344,496 B1 | 2/2002 | Niederauer et al. | |
| 6,365,132 B1 * | 4/2002 | Litkowski et al. | 424/49 |
| 6,416,745 B1 * | 7/2002 | Markowitz et al. | 424/49 |
| 6,423,343 B1 | 7/2002 | Lee et al. | |
| 6,663,878 B1 | 12/2003 | Greenspan et al. | |
| 6,689,341 B2 | 2/2004 | Galli | |
| 6,756,060 B1 | 6/2004 | Greenspan et al. | |
| 2004/0047814 A1 | 3/2004 | Xu et al. | |
| 2004/0086467 A1 | 5/2004 | Curro | |
| 2005/0142077 A1* | 6/2005 | Zimmer et al. | 424/57 |
| 2006/0008424 A1 | 1/2006 | MacDonald et al. | |
| 2007/0258916 A1 | 11/2007 | Ferracane et al. | |
| 2007/0264291 A1* | 11/2007 | Greenspan et al. | 424/401 |
| 2008/0161394 A1 | 7/2008 | Fouron et al. | |

(Continued)

FOREIGN PATENT DOCUMENTS

| | | |
|---|---|---|
| CA | 2728391 | 12/2009 |
| CN | 1290158 A | 4/2001 |

(Continued)

OTHER PUBLICATIONS

NovaMin, "In-vitro evaluation of NovaMin root conditioner", http://www.oralscience.ca/en/documentation/articles/tooth_paste/In-Vitro-Evaluation-of-NovaMin-Root-Conditioner.pdf, accessed Apr. 17, 2013.*
ISR & Written Opinion for PCT/US2010/029682 dated Apr. 3, 2012.
ISR & Written Opinion for PCT/US2010/029684 dated Apr. 4, 2012.
ISR & Written Opinion for PCT/US2010/029686 dated Apr. 3, 2012.
Merolli et al., Comparison in in-vivo response between a bioactive glass and a non-bioactive glass, Apr. 2000, pp. 219-222. Journal of Materials Science, vol. 11, No. 4, Kluwer Academic Publishers.
Tilocca et al., The Structure of Bioactive Silicate Glasses: New Insight from Molecular Dynamics Simulations, Jan. 2007, pp. 95-103, Chemistry of Materials, vol. 19, No. 1.

(Continued)

*Primary Examiner* — Melissa Fisher

(57) ABSTRACT

The invention encompasses combinations of bioactive glass composition and potassium salts that are useful in conjunction with delivery agent such as, for example, toothpastes, mouthwashes, and oral gels. In certain embodiments, the compositions of the invention form a rapid and continuous reaction with body fluids (e.g., saliva) to promote the immediate and long-tem release of Ca and P ions to produce a stable crystalline layer deposited onto and into the dentin tubules for the immediate and long term reduction of dentin hypersensitivity and tooth surface remineralization.

15 Claims, 4 Drawing Sheets

(56) References Cited

U.S. PATENT DOCUMENTS

| | | | |
|---|---|---|---|
| 2008/0176190 A1* | 7/2008 | Cook et al. | 433/216 |
| 2009/0092562 A1 | 4/2009 | Zaidel et al. | |
| 2009/0208428 A1 | 8/2009 | Hill et al. | |
| 2009/0324516 A1 | 12/2009 | Muscle et al. | |

FOREIGN PATENT DOCUMENTS

| | | |
|---|---|---|
| CN | 1562075 A | 1/2005 |
| CN | 101407373 | 4/2009 |
| DE | 102004050954 | 4/2006 |
| DE | 102005052400 | 5/2007 |
| EP | 0381445 | 8/1990 |
| EP | 0975284 | 2/2000 |
| EP | 1018978 | 7/2000 |
| EP | 1049457 | 11/2000 |
| EP | 1123072 | 8/2001 |
| EP | 0833602 | 9/2001 |
| EP | 1185247 | 3/2002 |
| EP | 1272144 | 1/2003 |
| EP | 0804136 | 5/2003 |
| EP | 1333796 | 8/2003 |
| EP | 0877716 | 10/2004 |
| EP | 1011621 | 6/2005 |
| EP | 1339381 | 10/2005 |
| EP | 0868903 | 11/2006 |
| EP | 1729722 | 12/2006 |
| EP | 1021148 | 5/2008 |
| EP | 1143919 | 10/2008 |
| JP | 10167942 | 6/1998 |
| RU | 2152778 | 7/2000 |
| RU | 2163798 | 3/2001 |
| RU | 2251405 | 5/2005 |
| WO | WO 96/010985 | 4/1996 |
| WO | WO 1997/027148 | 7/1997 |
| WO | WO 99/13852 | 3/1999 |
| WO | WO 01/72262 | 10/2001 |
| WO | WO 2002/015809 | 2/2002 |
| WO | WO 02/38119 | 5/2002 |
| WO | WO 05/063185 | 7/2005 |
| WO | WO 2006/055317 | 5/2006 |
| WO | WO 2007/051543 | 5/2007 |
| WO | WO 07/064885 | 6/2007 |
| WO | WO2007/144662 | * 12/2007 |
| WO | WO2007144662 | * 12/2007 |
| WO | WO 2008/074625 | 6/2008 |
| WO | WO 08/140936 | 11/2008 |
| WO | WO 09/158564 | 12/2009 |
| WO | WO 2010/115039 | 10/2010 |
| WO | WO 2011/050369 | 4/2011 |

OTHER PUBLICATIONS

Azouka et al., 1993, "The production of shellac and its general and dental uses: a review," J. Oral Rehabilitation 20:393-400.

Blixt et al., 1993, "The influence of lining techniques on the marginal seal of Class II composite resin restorations," Quintessence International 24(3):203-210.

Gorustovich et al., 2007, "Osteoconductivity of Strontium-Doped Bioactive Glass Particles," Bone 41(6):S4 Abstract.

Klineberg et al., 1967, "Physical properties of shellac baseplate materials," Australian Dental J. 12(5):468-475.

Kokubo, 1990, "Surface Chemistry of Bioactive Glass-Ceramics," J. of Non-Crystalline Solids 120:138-151.

Lee et al., 1991, "The effect of bead attachment systems on casting patterns and resultant tensile bond strength of composite resin veneer cast restorations," J. Prosthetic Dentistry 66(5):623-630.

Marini et al., "Pilot Clinical Study Evaluating Efficacy of NovaMin-Containing Dentifrice for Relief of Dentin Hypersensitivity," NovaMin Research Report.

Pashley et al., "Dentin permeability. Effects of desensitizing dentifrices in vitro," 1984, J. Periodontol. 55(9):522-525.

Zhang et al.,1998, "The effects of Pain-Free Desensitizer on dentine permeability and tubule occlusion over time, in vitro," J. Clin. Periodontol. 25(11 Pt. 1):884-891.

Wara-Aswapati et al., 2004, "The effect of a new toothpaste containing potassium nitrate and tricolsan on gingival health, plaque formation and dentine hypersensitivity." J. Clinical Periodontology 32:53-58.

Fechner, 2005, "Bioactive glasses as a potential new class of anti-oxidative ingredients for personal care products." SOFW Journal International Journal for Applied Science pp. 1-5.

Hager & Werken, 2007, "Nanosensitive hea," Mintel GNPD AN: 677422.

MEDINFLUX, 2006, "Tooth Sensitivity Treatment Toothpaste," Mintel GNPD AN: 601274.

Periproducts, 2009, "Toothpaste," Mintel GNPD AN: 1079067.

\* cited by examiner

DUAL ACTION DENTIFRICE COMPOSITIONS TO PREVENT HYPERSENSITIVITY AND PROMOTE REMINERALIZATION

CROSS-REFERENCE TO RELATED APPLICATIONS

The present application is a national stage entry under 35 U.S.C. § 371 of International patent application No. PCT/US2010/029684, filed Apr. 1, 2010, which claims priority to U.S. Provisional Application No. 61/165,749, filed Apr. 1, 2009, the entireties of which are hereby incorporated by reference.

FIELD OF THE INVENTION

The invention encompasses combinations of bioactive glass composition and potassium salts that are useful in oral care compositions, for example, toothpastes, mouthwashes, and oral gels. In certain embodiments, the compositions of the invention form a rapid and continuous reaction with body fluids (e.g., saliva) to promote the immediate and long-term release of calcium and phosphorus ions to produce a stable crystalline layer deposited onto and into the dentin tubules for the immediate and long term reduction of dentin hypersensitivity and tooth surface remineralization.

BACKGROUND OF THE INVENTION

Human tooth enamel naturally undergoes a process of demineralization. Exposure of enamel to saliva and food slowly leaches minerals from teeth and eventually leads to increased susceptibility to decay. This process of demineralization results in incipient caries, which are typically very small defects in the enamel surface. Carious dentin demineralization also may occur in patients that have exposed regions of dentin resulting from decay below the cementum-enamel junction. Accordingly, there has been much work associated with slowing this natural process of demineralization including the application of fluoride and other topical treatments.

The current inventors have identified novel compositions and methods useful in reducing dentin hypersensitivity and promoting tooth surface remineralization.

SUMMARY OF THE INVENTION

The invention generally encompasses oral care compositions including a combination of potassium salts and bioactive glass. Other embodiments of the invention encompass oral care compositions including a combination of potassium salts and calcium or phosphate salts. The potassium salts are present in the compositions of the invention in an amount effective to desensitize the nerves in the oral cavity, for example, nerves in the teeth, and the bioactive glass or the calcium and phosphate salts are present in the compositions of the invention in an amount effective to block dentin tubules, thereby preventing hypersensitivity.

In one embodiment, the invention encompasses dentifrice compositions including an effective amount of a bioactive and biocompatible glass and a desensitizing effective amount of a potassium salt.

In another embodiment, the invention encompasses methods for treating dental hypersensitivity comprising contacting one or more hypersensitive teeth in a subject in need thereof with an effective amount of a bioactive and biocompatible glass and a desensitizing effective amount of a potassium salt.

In another embodiment, the invention encompasses methods for at least partially occluding dentin tubules comprising contacting said tubules of a subject in need thereof with an effective amount of a bioactive and biocompatible glass and a desensitizing effective amount of a potassium salt.

In another embodiment, the invention encompasses methods for preventing tooth decay comprising contacting a tooth structure in a subject in need thereof with an effective amount of a bioactive and biocompatible glass and a desensitizing effective amount of a potassium salt.

In another embodiment, the invention encompasses methods for preventing incipient carries comprising contacting a tooth structure in a subject in need thereof with an effective amount of a bioactive and biocompatible glass and a desensitizing effective amount of a potassium salt.

In another embodiment, the invention encompasses methods for remineralizing enamel comprising contacting a tooth structure in a subject in need thereof with an effective amount of a bioactive and biocompatible glass and a desensitizing effective amount of a potassium salt.

In another embodiment, the invention encompasses methods for sealing fissures in tooth structure comprising contacting a tooth structure in a subject in need thereof with an effective amount of a bioactive and biocompatible glass and a desensitizing effective amount of a potassium salt.

In another embodiment, the invention encompasses methods for sealing pits in a tooth structure comprising contacting a tooth structure in a subject in need thereof with an effective amount of a bioactive and biocompatible glass and a desensitizing effective amount of a potassium salt.

In another embodiment, the invention encompasses methods for lining tooth structure comprising contacting a tooth structure in a subject in need thereof with an effective amount of at least one bioactive and biocompatible glass and a desensitizing effective amount of a potassium salt.

In another embodiment, the invention encompasses methods for capping pulp comprising contacting a tooth structure in a subject in need thereof with an effective amount of a bioactive and biocompatible glass and a desensitizing effective amount of a potassium salt.

In another embodiment, the invention encompasses methods for treating tooth structure in a subject in need thereof after periodontal surgery comprising contacting a tooth structure with an effective amount of a bioactive and biocompatible glass and a desensitizing effective amount of a potassium salt.

In another embodiment, the invention encompasses methods for preventing tooth decay comprising contacting a tooth structure in a subject in need thereof with an effective amount of a bioactive and biocompatible glass and a desensitizing effective amount of a potassium salt.

In another embodiment, the invention encompasses methods for treating tooth decay comprising contacting a tooth structure in a subject in need thereof with an effective amount of a bioactive and biocompatible glass and a desensitizing effective amount of a potassium salt.

In another embodiment, the invention encompasses methods for remineralizing enamel comprising contacting a tooth structure in a subject in need thereof with an effective amount of a bioactive and biocompatible glass and a desensitizing effective amount of a potassium salt.

In another embodiment, the invention encompasses methods for incipient caries remineralization comprising contacting a tooth structure in a subject in need thereof with an effective amount of a bioactive and biocompatible glass and a desensitizing effective amount of a potassium salt.

In another embodiment, the invention encompasses methods for sealing fissures in tooth structure comprising contacting a tooth structure in a subject in need thereof with an effective amount of a bioactive and biocompatible glass and a desensitizing effective amount of a potassium salt.

In one embodiment, the invention encompasses dentifrice compositions including an effective amount of calcium and phosphate salts and a desensitizing effective amount of a potassium salt.

In another embodiment, the invention encompasses methods for treating dental hypersensitivity comprising contacting one or more hypersensitive teeth in a subject in need thereof with an effective amount calcium and phosphate salts and a desensitizing effective amount of a potassium salt.

In another embodiment, the invention encompasses methods for at least partially occluding dentin tubules comprising contacting said tubules in a subject in need thereof with an effective amount of calcium and phosphate salts and a desensitizing effective amount of a potassium salt.

In another embodiment, the invention encompasses methods for preventing tooth decay comprising contacting a tooth structure in a subject in need thereof with an effective amount of calcium and phosphate salts and a desensitizing effective amount of a potassium salt.

In another embodiment, the invention encompasses methods for preventing incipient carries comprising contacting a tooth structure in a subject in need thereof with an effective amount of calcium and phosphate salts and a desensitizing effective amount of a potassium salt.

In another embodiment, the invention encompasses methods for remineralizing enamel comprising contacting a tooth structure in a subject in need thereof with an effective amount of calcium and phosphate salts and a desensitizing effective amount of a potassium salt.

In another embodiment, the invention encompasses methods for sealing fissures in tooth structure comprising contacting a tooth structure in a subject in need thereof with an effective amount of calcium and phosphate salts and a desensitizing effective amount of a potassium salt.

In another embodiment, the invention encompasses methods for sealing pits in tooth structure comprising contacting a tooth structure in a subject in need thereof with an effective amount of calcium and phosphate salts and a desensitizing effective amount of a potassium salt.

In another embodiment, the invention encompasses methods for lining tooth structure comprising contacting a tooth structure in a subject in need thereof with an effective amount of calcium and phosphate salts and a desensitizing effective amount of a potassium salt.

In another embodiment, the invention encompasses methods for capping pulp comprising contacting a tooth structure in a subject in need thereof with an effective amount of calcium and phosphate salts and a desensitizing effective amount of a potassium salt.

In another embodiment, the invention encompasses methods for treating tooth structure in a subject in need thereof after periodontal surgery comprising contacting a tooth structure with an effective amount of calcium and phosphate salts and a desensitizing effective amount of a potassium salt.

In another embodiment, the invention encompasses methods for preventing tooth decay comprising contacting a tooth structure in a subject in need thereof with an effective amount of calcium and phosphate salts and a desensitizing effective amount of a potassium salt.

In another embodiment, the invention encompasses methods for treating tooth decay comprising contacting a tooth structure in a subject in need thereof with an effective amount of calcium and phosphate salts and a desensitizing effective amount of a potassium salt.

In another embodiment, the invention encompasses methods for remineralizing enamel comprising contacting a tooth structure in a subject in need thereof with an effective amount of calcium and phosphate salts and a desensitizing effective amount of a potassium salt.

In another embodiment, the invention encompasses methods for incipient caries remineralization comprising contacting a tooth structure in a subject in need thereof with an effective amount of calcium and phosphate salts and a desensitizing effective amount of a potassium salt.

In another embodiment, the invention encompasses methods for sealing fissures in tooth structure comprising contacting a tooth structure in a subject in need thereof with an effective amount of calcium and phosphate salts and a desensitizing effective amount of a potassium salt.

DETAILED DESCRIPTION OF THE INVENTION

General Description

Figure 1:
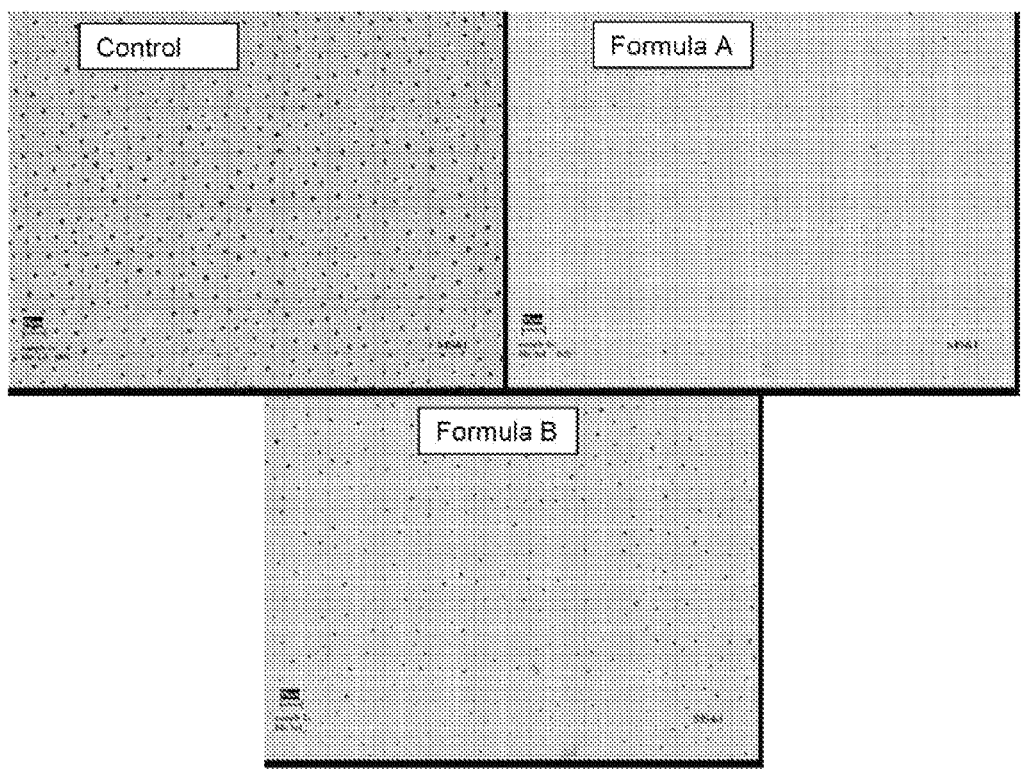
FIG. 1 depicts the results of scanning electron microscopy of dentinal samples treated with compositions of the invention versus control samples.

The invention generally encompasses dentifrice compositions including an effective amount of a bioactive and biocompatible glass or a combination of a calcium and phosphate salt; and a desensitizing effective amount of a potassium salt.

In certain embodiments, the potassium salt is potassium bicarbonate, potassium citrate, potassium chloride, or potassium nitrate.

In certain embodiments, the bioactive glass is calcium sodium phosphosilicate.

In certain embodiments, the bioactive and biocompatible glass has a particle size range of less than 90 μm.

In certain embodiments, the bioactive and biocompatible glass has a particle size range of less than 70 μm.

In certain embodiments, the bioactive and biocompatible glass has a particle size range of less than 50 μm.

In certain embodiments, the bioactive and biocompatible glass has a particle size range of less than 40 μm.

In certain embodiments, the bioactive and biocompatible glass has a particle size range of less than 30 μm.

In certain embodiments, the bioactive and biocompatible glass has a particle size range of less than 20 μm.

In certain embodiments, the potassium salt is present in an amount of 0.1 wt. % to 10 wt. % based on the total weight of the composition.

In certain embodiments, the potassium salt is present in an amount of 1 wt. % to 5 wt. % based on the total weight of the composition.

In certain embodiments, the potassium salt is present in an amount of 2 wt. % to 4 wt. % based on the total weight of the composition.

In certain embodiments, the potassium salt is present in an amount of 3.75 wt. % based on the total weight of the composition.

In certain embodiments, the bioactive and biocompatible glass includes the following composition by weight percentage:

| Ingred. | wt. % |
|---|---|
| $SiO_2$ | 40-60 |
| $CaO_2$ | 10-30 |
| $Na_2O$ | 10-35 |
| $P_2O_5$ | 2-8 |
| $CaF_2$ | 0-25 |
| $B_2O_3$ | 0-10 |
| $K_2O$ | 0-8 |
| $MgO$ | 0-5. |

In certain embodiments, the composition is a incorporated in toothpaste, glycerin gel or mouthwash.

In certain embodiments, the bioactive and biocompatible glass includes an effective dentin tubule occluding amount of particles less than 5 μm.

In certain embodiments, the bioactive and biocompatible glass includes an effective dentin tubule occluding amount of particles less than 2 μm.

In certain embodiments, the compositions further comprise one or more sources of fluoride.

In certain embodiments, the compositions further comprise one or more antibacterial agents.

In certain embodiments, the compositions further comprise one or more tartar control agents.

In certain embodiments, the compositions further comprise one or more structure building agents.

In certain embodiments, the bioactive and biocompatible glass is present in an amount of 0.1 wt. % to 20 wt. % based on the total weight of the composition.

In certain embodiments, the bioactive and biocompatible glass is present in an amount of 0.5 wt. % to 15 wt. % based on the total weight of the composition.

In certain embodiments, the bioactive and biocompatible glass is present in an amount of 1 wt. % to 10 wt. % based on the total weight of the composition.

In certain embodiments, the bioactive and biocompatible glass is present in an amount of 3 wt. % to 7 wt. % based on the total weight of the composition.

In certain embodiments, the bioactive and biocompatible glass is present in an amount of 5 wt. % based on the total weight of the composition.

In certain embodiments, the bioactive and biocompatible glass is present in an amount of 7.5 wt. % based on the total weight of the composition In certain embodiments, the compositions described herein are useful in methods for treating dental hypersensitivity; methods for at least partially occluding dentin tubules; methods for preventing tooth decay; methods for preventing incipient carries; methods for remineralizing enamel; methods for sealing fissures in tooth structure; methods for sealing pits in tooth structure; method for lining tooth structure; methods for capping pulp; methods for treating tooth structure; methods for preventing tooth decay; method for treating tooth decay; methods for remineralizing enamel; methods for incipient caries remineralization; methods for sealing fissures in tooth structure; and combinations thereof.

I. Compositions of the Invention

The present invention provides an oral care composition and methods for administration or application to, or use with, a human or other animal subject. The compositions of the invention include a biocompatible and bioactive glass and a desensitizing effective amount of a potassium salt, which compositions are useful in, for example, enamel remineralization, incipient caries remineralization, carious dentin remineralization, caries prevention, arresting decay, reversing decay, anti-caries, pit and fissure sealants, prophylactic pastes, fluoride treatments, dentinal sealants, and combinations thereof. Without being limited by theory, it is believed that the compositions of the invention are capable of providing a bioactive layer that will form a new structural layer, which is a lasting remineralization of tooth structure. This can be verified by the reformation of a hydroxycarbonate apatite layer on dentin surfaces after treatment with compositions in accordance with the present invention with Fourier Transform Infrared spectroscopy (FTIR).

The oral care compositions of the invention can also be included, for example, in toothpastes, mouthwashes, liners, bases, gels, and restorative material, for example, packing or indirect pulp capping agent. If the compositions are toothpastes, the composition can be delivered from a single or dual tube. The single tube option utilizes non-aqueous technology to deliver the occlusive ingredients so that they will precipitate on the tooth surface upon exposure to water/saliva in the mouth.

As referred to herein, an "oral care composition" is any composition that is suitable for administration or application to the oral cavity of a human or animal subject for enhancing the health, hygiene or appearance of the subject, for example, providing benefits such as: the prevention or treatment of a condition or disorder of the teeth, gums, mucosa or other hard or soft tissue of the oral cavity; the prevention or treatment of a systemic condition or disorder; the provision of sensory, decorative or cosmetic benefits; and combinations thereof.

Compositions in accordance with the invention are also useful in the treatment of surfaces after periodontal surgery to decrease dentinal sensitivity and enhance tissue attachment. The compositions are active in treating various defects associated with a variety of dental and other conditions and actually chemically and physically bond to the tooth thereby remineralizing tooth structure.

As referred to herein, the term "remineralization" is the formation of hydroxyapatite on a tooth surface. The formation of hydroxyapatite begins with exposure of a bioactive glass composition to aqueous solutions. Without being limited by theory, it is believed that the sodium ions ($Na^+$) in the bioactive glass exchanges with $H^+$ ions in body fluids causing pH to increase. Calcium and phosphorus then migrate from the bioactive glass forming a calcium-phosphorous rich surface layer. An underlying silica rich zone slowly increases as the sodium ion in the bioactive glass continues to exchange with the hydrogen ion of the solution. After time, the calcium-phosphorous rich layer crystallizes into a hydroxyapatite material. Collagen can become structurally integrated with the apatite agglomerates. As herein-after referred to, an effective remineralizing amount is any amount capable of forming hydroxyapatite.

The term "remineralizing effective amount" is an amount of hydroxyapatite effective to cause remineralization on a tooth surface.

As used herein, the term "a tooth structure" refers to any feature or features of a tooth including but not limited to enamel, dentin, pulp, tooth root structure, cementum, root dentin, coronal dentin, and any dental manufacture or combinations thereof. As referred to herein, "tooth" or "teeth" refers to natural teeth, dentures, dental plates, fillings, caps, crowns, bridges, dental implants, and the like, and any other hard surfaced dental prosthesis either permanently or temporarily fixed within the oral cavity.

1. Bio-Acceptable and Bioactive Glass

The compositions of the invention generally include one or more bio-acceptable, bioactive glasses.

Suitable bioacceptable and bioactive glasses for use in the invention include, but are not limited to, an inorganic glass material capable of forming a layer of hydroxycarbonate apatite in accordance with the present invention. In one embodiment, the dentifrice composition of the present invention includes a bioactive and bioacceptable glass. In one embodiment, the composition includes calcium sodium phosphosilicate. In one embodiment, the composition includes calcium sodium phosphosilicate in an amount from 1.0 wt. % to 20 wt. %. In one embodiment, the composition includes calcium sodium phosphosilicate in an amount from 5.0 wt. % to 15 wt. %. In one embodiment, the composition includes calcium sodium phosphosilicate in an amount of 10 wt. %.

Suitable bioacceptable and bioactive glasses may have compositions including: from 40 wt. % to 86 wt. % of silicon dioxide ($SiO_2$); from 0 wt. % to 35 wt. % of sodium oxide ($Na_2O$); from 4 wt. % to 46 wt. % of calcium oxide (CaO); and from 1 wt. % to 15 wt. % of phosphorus oxide ($P_2O_5$). Preferably, the bioacceptable and bioactive glass includes: from 40 wt. % to 60 wt. % of silicon dioxide ($SiO_2$); from 10 wt. % to 30 wt. % of sodium oxide ($Na_2O$); from 10 wt. % to 30 wt. % of calcium oxide (CaO); and from 2 wt. % to 8 wt. % of phosphorus oxide ($P_2O_5$). The oxides may be present as solid solutions or mixed oxides, or as mixtures of oxides. Exemplary bioacceptable and bioactive glass suitable for use in the present invention include NovaMin®, which has a composition including 45 wt. % of silicon dioxide, 24.5 wt. % of sodium oxide, 6 wt. % of phosphorus oxide, and 24.5 wt. % of calcium oxide.

In one embodiment, the composition of suitable bioacceptable and bioactive glass may also include: $CaF_2$, $B_2O_3$, $Al_2O_3$, MgO and $K_2O$, in addition to silicon, sodium, phosphorus and calcium oxides. In certain embodiments, the range of $CaF_2$ is from 0 wt. % to 25 wt. %. The preferred range for $B_2O_3$ is from 0 wt. % to 10 wt. %. The preferred range for $Al_2O_3$ is from 0 wt. % to 4 wt. %. The preferred range for MgO is from 0 wt. % to 5 wt. %. The preferred range for $K_2O$ is from 0 wt. % to 8 wt. %.

In certain embodiments, small-particle silica boosts efficacy and is a useful pH adjuster to bring down alkalinity caused by, for example, Novamin.

An "effective" amount of the bio-acceptable and bioactive glass is an amount that is sufficient to have the desired therapeutic or prophylactic effect in the human or lower animal subject to whom the active is administered, without undue adverse side effects (such as toxicity, irritation, or allergic response), commensurate with a reasonable benefit/risk ratio when used in the manner of this invention. The specific effective amount will vary with such factors as the particular condition being treated, the physical condition of the subject, the nature of concurrent therapy (if any), the specific active used, the specific dosage form, the carrier employed, and the desired dosage regimen.

The bioactive glasses of the invention provide an efficacious material for interaction with the tooth structure. A biocompatible glass in accordance with the invention is one that does not trigger an adverse immune response.

In accordance with the invention, it has been found that bioactive glasses of specified particle sizes are particularly useful in treating the above-mentioned conditions. Specifically, surprising results are obtained by the compositions of the invention where small and very small particles are combined. In certain embodiments, for example, the bioactive glass portion of the compositions include small particles that are capable of bonding with tooth structure (e.g., less than 90 microns) as well smaller particles (e.g., less than 10) are used in combination, the larger of these particles adhere to tooth structure and act as ionic reservoirs while the smaller are capable of entering and lodging inside of various tooth structure surface irregularities.

In one embodiment, bioacceptable and bioactive glass suitable for use in the present invention is particulate, non-interlinked bioactive glass. In one embodiment, the glass has a particle size range of less than 90 μm. In one embodiment, the glass has a particle size range of less than 70 μm. In one embodiment, the glass has a particle size range of less than 50 μm. In one embodiment, the glass has a particle size range of less than 40 μm. In one embodiment, the glass has a particle size range of less than 30 μm. In one embodiment, the glass has a particle size range of less than 20 p.m. In certain embodiments, the particle size of the bioactive glass portion of the compositions is less than 20, 10, 5, 4, 3, 2, 1 micron.

In an embodiment, a glass has a median particle size between 0.5 μm and 90 μm. In another embodiment, a glass has median a particle size between 0.5 μm and 70 μm. In another embodiment, a glass has a median particle size between 0.5 μm and 50 μm. In another embodiment, a glass has a median particle size between 0.5 μm and 40 μm. In another embodiment, a glass has a median particle size between 0.5 μm and 30 μm. In another embodiment, a glass has a median particle size between 0.5 μm and 20 μm. In another embodiment, a glass has a median particle size between 0.5 μm and 10 μm. In another embodiment, a glass has a median particle size between 0.5 μm and 5 μm. In another embodiment, a glass has a median particle size between 0.5 μm and 4 μm. In another embodiment, a glass has a median particle size between 0.5 μm and 3 μm. In another embodiment, a glass has a median particle size between 0.5 μm and 2 μm. In another embodiment, a glass has a median particle size between 0.5 μm and 1 μm. In yet another embodiment, a glass has a median particle size selected from the group consisting of 0.5 μm, 1 μm, 2 μm, 3 μm, 4 μm, 5 μm, 7.5 μm and 10 μm.

In certain embodiments, the larger of these particles (e.g., less than 90 microns to less than 20 microns) provide a reservoir of additional calcium and phosphorous so that the mineralization, or depositing of the calcium phosphate layer begun by the small particles (e.g., less than 20 microns to less than 1 micron) can continue. In certain embodiments of the invention, additional calcium and phosphorous can be leached to all tooth structure as well as to particles, which have become attached to the inside or at the openings of surface irregularities of tooth structure such as dentinal tubules. This in turn provides for continuation of the entire reaction and continued growth of the smaller of these particles, which have lodged inside or over the openings of such surface irregularities and can result in effectively coating or filling the surface irregularity. This excess concentration of ions of calcium and phosphorous allows reaction of the smaller of these particles to take place because the smaller particles quickly exhaust their ions because of their relatively high surface area. The larger of these particles will react and release their ions more slowly as a longer term effect. Furthermore, the larger of these particles will mechanically abrade the tooth surface opening various surface irregularities allowing small particles to enter and react with the surface irregularity.

This effect is very beneficial in a variety of applications. For example, in preventing caries or decay, the compositions of the invention are capable of penetrating into the depths of the smallest of surface irregularities and receiving a continued supply of ions from larger nearby particles so that it is able to grow after exhausting its stored ion supply. This is also very useful in sealing pits and fissures, and a much more effective and long lasting seal is obtained.

The occlusion of these tubules leads to a significant reduction in the amount of sensitivity after, for example, periodontal surgery. In certain embodiments, a mixture of particles less than two microns and larger than 45 microns in diameter are used. It has been found that this combination yields a particularly effective composition.

In certain embodiments, the bioactive and biocompatible glass encompasses glass includes the following compositions by weight percentage:

| Ingred. | wt. % |
|---|---|
| $SiO_2$ | 40-60 |
| $CaO_2$ | 10-30 |
| $Na_2O$ | 10-35 |
| $P_2O_5$ | 2-8 |
| $CaF_2$ | 0-25 |
| $B_2O_3$ | 0-10. |

In certain embodiments, the following composition by weight percentage encompasses a bioactive glass:

| Ingred. | wt. % |
|---|---|
| $SiO_2$ | 40-60 |
| $CaO_2$ | 10-30 |
| $Na_2O$ | 10-35 |
| $P_2O_5$ | 2-8 |
| $CaF_2$ | 0-25 |
| $B_2O_3$ | 0-10 |
| $K_2O$ | 0-8 |
| MgO | 0-5. |

2. Potassium Salts of the Invention

The potassium salts of the invention include water-soluble sources of potassium ions including, but not limited to, potassium nitrate, potassium citrate, potassium bicarbonate, or combinations thereof Without being limited by theory, the water-soluble potassium salts, which produce potassium ions act directly on exposed tooth dentin.

In certain embodiments, potassium salts have the surprising effect of building structure/viscosity in the system.

In certain embodiments, the amount of potassium salts in the compositions of the invention is an amount effective for desensitizing sensitive teeth. For example, the potassium salt is used in an amount, calculated as potassium, of 0.1 wt. % to 10 wt. %, 0.7 wt. % to 3 wt. %, 1.5 wt. % to 2.3 wt. %, by weight of the composition.

3. Calcium Salts of the Invention

The calcium salts of the invention include water-soluble sources of calcium ions including, but not limited to, calcium chloride, calcium carbonate, or combinations thereof Without being limited by theory, the water-soluble calcium salts, which produce calcium ions act directly on exposed tooth dentin In certain embodiments, the amount of calcium salts in the compositions of the invention is an amount effective for mineralizing teeth and/or blocking dentin tubules. For example, the calcium salt is used in an amount of 0.1 wt. % to 10 wt. %, 0.7 wt. % to 5 wt. %, 1.5 wt. % to 4 wt. %, or 3 wt. % by weight of the composition.

4. Phosphate Salts of the Invention

The phosphate salts of the invention include water-soluble sources of phosphate ions including, but not limited to, sodium phosphate dibasic, calcium phosphate, or combinations thereof. Without being limited by theory, the water-soluble phosphate salts, which produce phosphate ions act directly on exposed tooth dentin In certain embodiments, the amount of phosphate salts in the compositions of the invention is an amount effective for mineralizing teeth and/or blocking dentin tubules. For example, the phosphate salt is used in an amount of 0.1 wt. % to 10 wt. %, 0.7 wt. % to 5 wt. %, 1.5 wt. % to 3 wt. %, or 2.5 wt. % by weight of the composition.

II. Other Ingredients in the Compositions of the Invention

In certain embodiments, the non-aqueous dentifrice composition of the invention may include any another additive conventionally used in dentifrice formulations. Any suitable additive in any suitable amount or form may be used. Suitable additives for use in the invention include, but are not limited to: surfactants, desensitizing agents including potassium salts, fluorine sources, whitening agents, tartar control agents, antibacterial agents, abrasives including silica, binders and thickening agents, detergents, adhesion agents, foam modulators, pH modifying agents, mouth-feel agents, sweeteners, flavorants, colorants, preservatives, combinations thereof, and the like. It is to be understood that these additives are optional components and can be, individually or collectively, excluded from the automatic dishwashing composition of the present invention. It is further understood that while general attributes of each of the above categories of materials may differ, there may be some common attributes and any given material may serve multiple purposes within two or more of such categories of materials. In certain embodiments, such additives are selected for compatibility with the bioactive glass and with other ingredients of the composition.

1. Surfactants

Surfactants suitable for use in the invention include but are not limited to: anionic surfactants, nonionic surfactants, cationic surfactants, amphoteric surfactants, ampholytic surfactants, zwitterionic surfactants, and mixtures thereof, as known to one of ordinary skill in the art. Suitable surfactants may be added in any suitable amount or form, may optionally be in a surfactant system, and may be added to provide any desired properties including, but not limited to, cleaning and/or foaming properties. Suitable surfactants may include anionic, cationic, nonionic and amphoteric surfactants.

In one embodiment, a dentifrice composition of the present invention includes at least one surfactant. In one embodiment, a composition including at least one surfactant includes sodium lauryl sulfate. In one embodiment, a composition includes sodium lauryl sulfate in an amount from 0.5 wt. % to 10 wt. %. In one embodiment, a composition includes sodium lauryl sulfate in an amount from 1 wt. % to 5 wt. %. In one embodiment, a composition includes sodium lauryl sulfate in an amount from 1.5 wt. % to 2 wt. %.

In one embodiment, a dentifrice composition of the invention including at least one surfactant includes a poloxamer. In one embodiment, a composition including a poloxamer includes an ethylene oxide/propylene oxide copolymer. In one embodiment, a composition including a poloxamer includes an ethylene oxide/propylene oxide copolymer in an amount from 1.0 wt. % to 45.0 wt. %. In one embodiment, a composition including a poloxamer includes an ethylene oxide/propylene oxide copolymer in an amount from 5.0 wt. % to 35.0 wt. %. In one embodiment, a composition including a poloxamer includes an ethylene oxide/propylene oxide copolymer in an amount from 10.0 wt. % to 25.0 wt. %.

2. Tartar Control Agent

In some embodiments, compositions of the invention may optionally comprise a tartar control (anti-calculus) agent formulated to not interfere with the efficacy of the bioactive glass and/or potassium salts described in detail herein. Tartar control agents among those useful herein include salts of any of these agents, for example their alkali metal and ammonium salts: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof.

3. Fluoride Sources

Fluoride sources suitable for use in the present invention may include any orally acceptable particulated fluoride-ion containing agent formulated to not interfere with the efficacy of the bioactive glass, and that may be useful, for example, as an anti-caries agent. Suitable fluorine sources may include, but are not limited to: ionic fluorides including alkali metal fluorides; amine fluorides such as olaflur (N'-octadecyltrimethylendiamine-N,N,N'-tris(2-ethanol)-dihydrofluoride); stannous fluoride; indium fluoride; and ionic monofluorophosphates including alkali metal monofluorophosphates such as potassium, sodium and ammonium fluorides and monofluorophosphates; and mixtures thereof.

In one embodiment, a dentifrice composition of the present invention further includes a fluorine source. In one embodiment, a composition further includes a fluoride salt. In one embodiment, a composition further including a fluoride salt includes sodium monofluorophosphate. In one embodiment, calcium glycerophosphate, which has been shown to enhance the activity of ionic monofluorophosphates, may be optionally added when the fluoride source is an ionic monofluorophosphate. In one embodiment, a composition may include a fluorine source providing between 100 and 3000 ppm of fluoride. In one embodiment, a composition may include a fluorine source providing between 500 and 2000 ppm of fluoride.

4. Whitening Agents

Whitening agents suitable for use in the present invention may include any therapeutically effective agent suitable for use in an oral cavity. Suitable whitening agents include, but are not limited to: titanium dioxide, hydrogen peroxide, sodium tripolyphosphate, and the like. In one embodiment, a dentifrice composition of the present invention further includes a whitening agent. In one embodiment, a composition of the present invention further includes titanium dioxide. In one embodiment, titanium dioxide may be included at appropriate levels.

5. Abrasives

Abrasives suitable for use in the present invention may include any orally acceptable particulated agent formulated to not interfere with the efficacy of the bioactive glass. Suitable abrasives for use in the present invention may include, but are not limited to: silica, zinc orthophosphate, sodium bicarbonate (baking soda), plastic particles, alumina, hydrated alumina, calcium carbonate, calcium pyrophosphate, and mixtures thereof. The silica abrasive may be a natural amorphous silica including diatomaceous earth; or a synthetic amorphous silica such as a precipitated silica; or a silica gel, such as a silica xerogel; or mixtures thereof.

Generally, an amount of abrasive suitable for use in the dentifrice composition of the invention will be empirically determined to provide an acceptable level of cleaning and polishing, in accordance with the techniques well known in the art. In one embodiment, a dentifrice composition of the present invention includes an abrasive. In one embodiment, a composition includes a silica abrasive. In one embodiment, a silica abrasive is present in an amount of from 1 wt. % to 30 wt. %. In one embodiment, a silica abrasive is present in an amount of from 5 wt. % to 15 wt. %. In one embodiment, a silica abrasive is present in an amount of from 7 wt. % to 10 wt. %.

6. Mouth-Feel Agents

Mouth-feel agents suitable for use in the present invention may include any orally acceptable materials imparting a desirable texture or other feeling during use of the dentifrice composition, in any form or amount. Suitable mouth-feel agents may include, but are not limited to: dispersed flavorants, sweeteners, saliva-stimulating agents, and the like.

Flavorants among those useful herein include any material or mixture of materials operable to enhance the taste of the composition. Any orally acceptable natural or synthetic flavorant can be used, such as flavoring oils, flavoring aldehydes, esters, alcohols, similar materials, and combinations thereof. Flavorants include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavorants herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, alpha-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA), and mixtures thereof. One or more flavorants are optionally present in a total amount of 0.01% to 5%, optionally in various embodiments from 0.05 to 2%, from 0.1% to 2.5%, and from 0.1 to 0.5%.

Sweeteners among those useful herein include orally acceptable natural or artificial, nutritive or non-nutritive sweeteners. Such sweeteners include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones, and mixtures thereof. One or more sweeteners are optionally present in a total amount depending strongly on the particular sweetener(s) selected, but typically at levels of from 0.005% to 5%, optionally from 0.01% to 1%.

The compositions of the present invention may optionally comprise a saliva stimulating agent formulated to not interfere with the efficacy of the bioactive glass and/or potassium salts described in detail herein and useful, for example, in amelioration of dry mouth. One or more saliva stimulating agents are optionally present in saliva stimulating effective total amount.

7. Other Actives

In some embodiments, compositions of the invention may optionally include other active materials, operable for the prevention or treatment of a condition or disorder of hard or soft tissue of the oral cavity, or the prevention or treatment of a physiological disorder or condition. In some embodiments, the active is a "systemic active" which is operable to treat or prevent a disorder that, in whole or in part, is not a disorder of the oral cavity. In some embodiments, the active is an "oral care active" operable to treat or prevent a disorder or provide a cosmetic benefit within the oral cavity (e.g., to the teeth, gingiva or other hard or soft tissue of the oral cavity). Oral care actives among those useful herein include whitening agents, anticaries agents, tartar control agents, antiplaque agents, periodontal actives, abrasives, breath freshening agents, tooth desensitizers, salivary stimulants, and combinations thereof.

In some embodiments, compositions of the invention may optionally include an antibacterial agent formulated to not interfere with the efficacy of the bioactive glass and/or potassium salts described in detail herein. Examples of antibacterial agents include, but are not limited to, triclosan, cetylpyridinium chloride, and combinations thereof.

In some embodiments, compositions of the invention include comprise a nutrient formulated to not interfere with the efficacy of the bioactive glass and/or potassium salts described in detail herein. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophane, L-lysine, methionine, threonine, levocarnitine and L-carnitine), lipotropics (such as choline, inositol, betaine, and linoleic acid), and mixtures thereof.

In some embodiments, compositions of the invention may also contain an antistain agent. Suitable antistain agents may include, but are not limited to: carboxylic acids, amino carboxylate compounds, phosphonoacetic acid, polyvinylpyrrolidone, and the like. The antistain agent may be incorporated into the dentifrice composition or may be provided as a separate composition, for use after the dentifrice.

In some embodiments, compositions of the invention may also include an agent to enhance surface deposition/retention of the bioglass and any resulting HAP deposits including, but not limited to, Gantrez, amelogenin, milk proteins (casein), chitosan, pluracare L1220 (ethylene oxide/propylene oxide copolymer), polyox, PVP, methacrylates, shellac, arginine, and combination thereof.

III. Methods of Treating and Preventing Disorders of the Oral Cavity

The dentifrice compositions of the invention include, in part, compositions including a bioacceptable and bioactive glass and one or more potassium salts that are useful in treating or preventing various disorders of the oral cavity in a subject in need thereof, for example, enamel remineralization, incipient caries remineralization, carious dentin remineralization, caries prevention, arresting decay, reversing decay, anti-caries, pit and fissure sealants, prophylactic pastes, fluoride treatments, dentinal sealants, and combinations thereof. As used herein, the term "subject" includes mammals, for example, humans and companion animals including cats and dogs.

In other embodiments, the dentifrice compositions of the invention include, in part, compositions including a calcium and phosphate salts and one or more potassium salts that are useful in treating or preventing various disorders of the oral cavity in a subject in need thereof, for example, enamel remineralization, incipient caries remineralization, carious dentin remineralization, caries prevention, arresting decay, reversing decay, anti-caries, pit and fissure sealants, prophylactic pastes, fluoride treatments, dentinal sealants, and combinations thereof.

Additional methods of treating or preventing disorders of the oral cavity are also included within the scope of the invention. In one embodiment, a method of at least partially occluding dentin tubules includes contacting the teeth or a tooth surface in a subject in need thereof with a non-aqueous dentifrice composition in accordance with the present invention. In one embodiment, a method of preventing tooth decay includes contacting the teeth or a tooth surface in a subject in need thereof with a non-aqueous dentifrice composition in accordance with the present invention. In one embodiment, a method of treating tooth decay includes contacting the teeth or a tooth surface in a subject in need thereof with a non-aqueous dentifrice composition in accordance with the present invention. In one embodiment, a method of preventing incipient carries includes contacting the teeth or a tooth surface in a subject in need thereof with a non-aqueous dentifrice composition in accordance with the present invention. In one embodiment, a method of remineralizing enamel includes contacting the teeth or a tooth surface in a subject in need thereof with a non-aqueous dentifrice composition in accordance with the present invention. In one embodiment, a method of sealing fissures includes contacting the teeth or a tooth surface in a subject in need thereof with a non-aqueous dentifrice composition in accordance with the present invention. In one embodiment, a method of sealing pits includes contacting the teeth or a tooth surface with a non-aqueous dentifrice composition in accordance with the present invention. In one embodiment, a method of lining tooth structure includes contacting the teeth or a tooth surface in a subject in need thereof with a non-aqueous dentifrice composition in accordance with the present invention. In one embodiment, a method for capping pulp includes contacting the teeth or a tooth surface in a subject in need thereof with a non-aqueous dentifrice composition in accordance with the present invention. In one embodiment, a method for treating tooth structure after periodontal surgery in a subject in need thereof includes contacting the teeth or a tooth surface with a non-aqueous dentifrice composition in accordance with the present invention.

IV. Method of Processing a Non-Aqueous Dentifrice Composition with Bioacceptable and Bioactive Glass The following procedure was followed for each exemplary dentifrice composition containing bioacceptable and bioactive glass and potassium salts.

1. A formula amount of glycerin was loaded to a suitable beaker. Saccharin, titanium dioxide, and potassium chloride were slowly added and mixed until well-dispersed. The beaker and contents were heated to 150° F. and mixed for fifteen (15) minutes.

2. Pluracare® L1220 PEG/PPG co-polymer was added to the ross mixer pot. The contents of the beaker in Step 1 were transferred to the ross pot and mixed for five (5) minutes with vacuum. After that time, the ross cover was opened and the temperature was checked. If the temperature was over 120° F., Step 2 was repeated. When the temperature cools to 120° F. or below, the sodium monofluorophosphate (MFP), bioactive glass (NovaMin®), silica thickener (Zeodent® 165) and silica abrasive (Zeodent® 114) were added, then mixed until the powders were wet. The vacuum was pulled, and the contents in the ross pot mixed for twenty (20) minutes on high speed.

3. The temperature was checked. The temperature should be 110° F. or below. Flavor and sodium lauryl sulfate powder was added, and then the composition mixed on ten (10) minutes on high speed under full vacuum.

EXAMPLES

The following examples illustrate illustrative compositions of the invention. Unless otherwise specified, all percentages are by weight. The exemplified compositions are illustrative only and do no limit the scope of the invention. It will be understood by those of skill in the art that numerous and various modifications can be made without departing from the spirit of the present invention. Therefore, it should be clearly understood that the forms of the present invention described herein are illustrative only and are not intended to limit the scope of the invention.

Example 1

Those of ordinary skill in the art will appreciate that the dentifrice compositions of the invention can be formulated using methods known in the art.

Table 1 describes a formulation with a bioactive glass and potassium chloride. In this illustrative example, a non-aqueous formula was prepared, in which the bioactive glass and potassium chloride were suspended. When the formula contacts water/saliva in the mouth, the potassium chloride and bioactive glass dissolve. The dissolved calcium and phosphate in the bioactive glass matrix can then react to form a precipitate that can block dentinal tubules. The potassium chloride salt can be dissolved in the glycerin in the formulation with slight heating:

TABLE 1

| Non-aqueous Toothpaste with Bioactive Glass (Formula A) | |
|---|---|
| Ingredients | Wt. % |
| Glycerin | 58.8 |
| Bioactive Glass (Novamin ®) | 5 |
| Pluracare L1220 | 5 |
| Saccharin | 0.3 |
| Zeodent 115 Silica | 20 |
| Zeodent 165 Silica | 3 |

TABLE 1-continued

| Non-aqueous Toothpaste with Bioactive Glass (Formula A) | |
|---|---|
| Ingredients | Wt. % |
| KCl | 3.7 |
| MFP | 1.1 |
| SLS Powder | 1.2 |
| Titanium Dioxide | 1 |
| Flavor | 0.8 |
| Total (wt. %) | 100 |

Example 2

A similar approach can be used where calcium chloride and sodium phosphate salts are used in place of the bioactive glass in the non-aqueous formula. Upon contact with water/saliva in the mouth, the calcium chloride and sodium phosphate react and precipitate calcium phosphate on the tooth to block dentinal tubules. An example of a formula is described in Table 2 below. The calcium chloride, sodium phosphate, and potassium chloride salts can be dissolved in glycerin in the formula with slight heating.

TABLE 2

| Non-aqueous Toothpaste with Calcium Phosphate (Formula B) | |
|---|---|
| Ingredients | Wt. % |
| Glycerin | 60 |
| Calcium chloride | 3 |
| $Na^+$ phosphate dibasic | 2.5 |
| Pluracare L1220 | 5 |
| Saccharin | 0.3 |
| Zeodent 115 Silica | 18.3 |
| Zeodent 165 Silica | 3 |
| KCl | 3.7 |
| MFP | 1.1 |
| SLS Powder | 1.2 |
| Titanium Dioxide | 1 |
| Flavor | 0.8 |
| Total (wt. %) | 100 |

Example 3

Etched dentin discs were brushed 14 times for 45 seconds with either Formula A or B and soaked in phosphate buffer between treatments. Another set of discs was brushed with phosphate buffer only (control). Discs were evaluated with an electron spectroscopy for chemical analysis ("ESCA") and scanning electron microscope ("SEM") to determine if an occlusive deposit formed. As shown below in Table 3 both Formula A and B showed significant deposition of calcium phosphate in ESCA (high Ca, P, and O levels) and substantial dentinal occlusion in SEM. FIG. 1 illustrates the SEM results.

TABLE 3

| ESCA Results | | | |
|---|---|---|---|
| | Atomic Percent | | |
| Sample | Ca | P | O |
| Buffer Control | 0.9 | 0.7 | 22..4 |
| Formula A | 8.0 | 6.3 | 40.3 |
| Formula B | 7.4 | 5.6 | 39.3 |

It is noteworthy that fluoride was stable and recoverable in Formulas A and B after aging them at elevated temperatures. After aging for 4 weeks at 40° C., 95% and 82% of the initial fluoride was recovered in Formulas A and B, respectively. The non-aqueous formulations prevent fluoride from dissolving and reacting with calcium and precipitating insoluble $CaF_2$ while the formula is on the shelf Example 4

In addition to potential anti-sensitivity benefits from potassium salts, the potassium unexpectedly helps thicken the non-aqueous bioactive glass formula. Below is a comparison of illustrative embodiments of compositions and viscosities of formulas prepared with and without potassium chloride. Formula A with 3.7% potassium chloride shows acceptable viscosity. However, with the potassium chloride is removed from the formula (Formula B), the viscosity drops dramatically and is unacceptable. In addition increasing the silica thickener does not improve the viscosity (Formula C).

TABLE 4

Non-aqueous Toothpaste with Bioactive Glass

| Ingredients | Formula A | Formula B | Formula C |
| --- | --- | --- | --- |
| Glycerin | 58.8 | 62.6 | 55.6 |
| Bioactive Glass (Novamin ®) | 5 | 5 | 5 |
| Pluracare L1220 | 5 | 5 | 5 |
| Saccharin | 0.3 | 0.3 | 0.3 |
| Zeodent 115 Silica | 20 | 20 | 20 |
| Zeodent 165 Silica (thickener) | 3 | 3 | 10 |
| KCl | 3.7 | 0 | 0 |
| MFP | 1.1 | 1.1 | 1.1 |
| SLS Powder | 1.2 | 1.2 | 1.2 |
| Titanium Dioxide | 1 | 1 | 1 |
| Flavor | 0.8 | 0.8 | 0.8 |
| Total (wt. %) | 100 | 100 | 100 |
| Brookfield Viscosity (>1 wk) | 26 | 4 | 6 |

Example 5

Single-Tube Toothpaste Product Including Occlusion Agent(s) and Potassium salt(s) That Offers Superior Tooth Sensitivity Relief An illustrative embodiment of the invention encompasses a single tube toothpaste product including one or more inclusion agents and one or more potassium salts. In one illustrative embodiment, to deliver faster relief, a single tube technology that combines rapid occlusion agents, for example, a bioactive and bio-acceptable glass (e.g., Novamin) with potassium is made. The non-aqueous bioactive and bio-acceptable glass formulations with potassium were found to provide significant in vitro occlusion.

In another illustrative embodiment, the bioactive and bio-acceptable glass (e.g., Novamin) formula is surprising found to possess additional occlusion benefit by adding commercially available small particle silica (e.g., Sorbosil AC-43).

Figure 2:
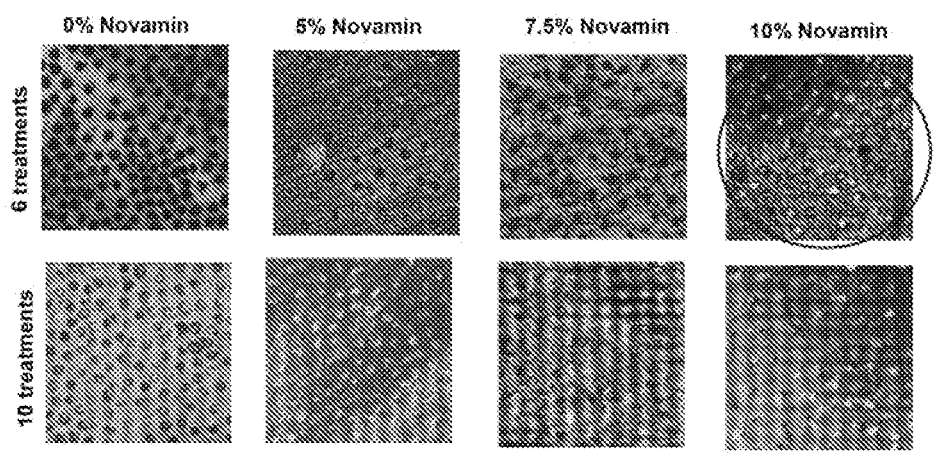
FIG. 2 depicts the results of an in vitro dose response study to determine the optimal bioactive and bio-acceptable glass level for rapid occlusion of tubules.

An in vitro dose response study was performed to determine the optimal bioactive and bio-acceptable glass (e.g., Novamin) level for rapid occlusion (FIG. 2). Products with the bioactive and bio-acceptable glass (e.g., Novamin) at 5%, 7.5% and 10% were prepared. Products were evaluated by confocal microscopy after 6 and 10 brushings. After six treatments, the 10% bioactive and bio-acceptable glass (e.g., Novamin) formula showed significant occlusion while all bioactive and bio-acceptable glass (e.g., Novamin) levels provided significant occlusion after 10 treatments.

To boost the 5% bioactive and bio-acceptable glass (e.g., Novamin) occlusion at six treatments, the effect of addition of silica (e.g., Ineos AC43 silica) was studied in vitro. As shown in the confocal microscopy images below, the addition of 9% silica (e.g., Ineos AC43 silica) significantly improved occlusion at six treatments.

Figure 3:
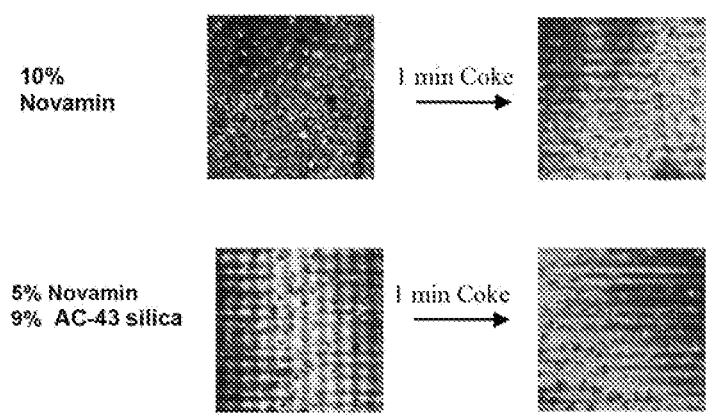
FIG. 3 depicts the acid resistance of the two systems set forth herein, as tested in vitro.

The acid resistance of the two leading systems was evaluated in vitro. The 6-treatment dentin disks were soaked for 1 minute in Coke Classic. Images are shown in FIG. 3. Both systems showed significant resistance to acid challenge.

To add body and prevent separation, various gums were added to the non-aqueous glycerin based formulas. In certain embodiments, carboxymethylcellulose provided the best overall mouthfeel. Carbopol provided body, but in certain embodiments imparted a sticky feel. The formulas were optimized. All lead formulas were stabile at 4 weeks at 40° C.

10% Novamin/20% Pluraflo/CMC (no KCl)
10% Novamin/3.75% KCL/CMC
5% Novamin/3.75% KCL/9% AC43/CMC Example 6

Figure 4:
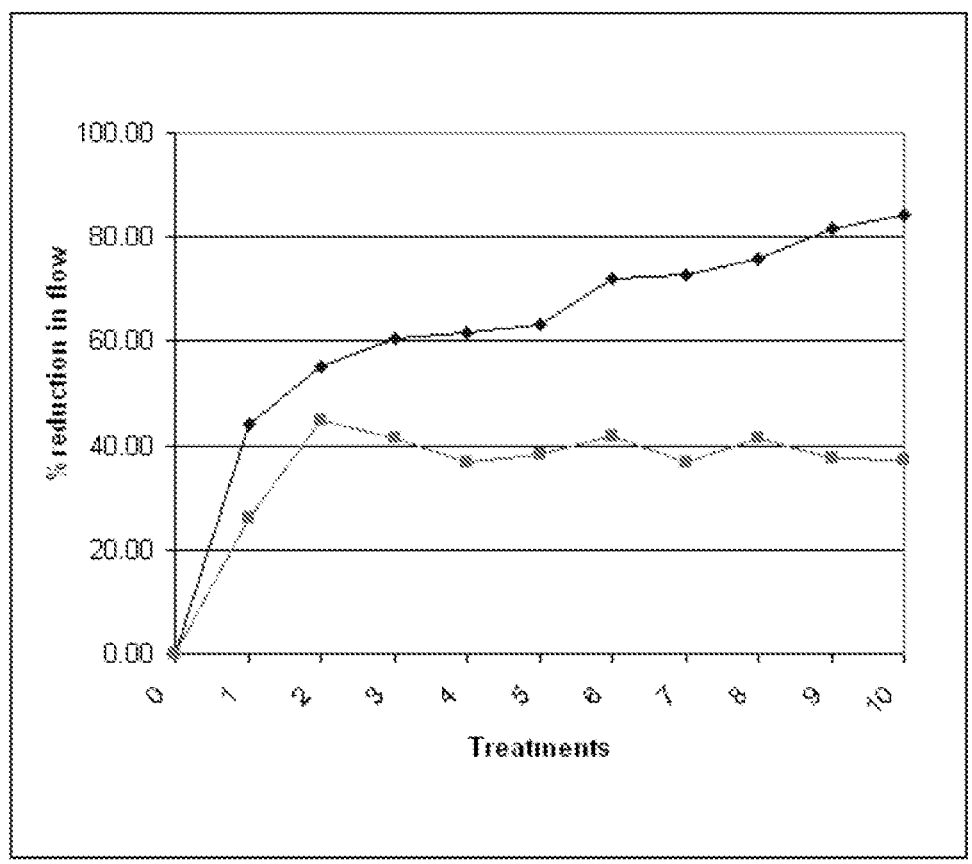
FIG. 4 depicts the results of conductance experiments with 10% Novamin toothpaste vs. conventional non-occlusion silica toothpaste control. Confocal laser microscopy images illustrate Novamin dose response and the boosting effect of AC43 silica. The top line represents Novamin, the bottom line represents the control sample.

Illustrated in FIG. 4 is conductance data with 10% Novamin toothpaste vs. conventional non-occlusion silica toothpaste control and confocal laser microscopy images showing Novamin dose response and boosting effect of AC43 silica. The top line represents Novamin, while the bottom line is the control.

| | Average Conductance | | | |
| --- | --- | --- | --- | --- |
| Treatments | % reduction Novamin 10% | stdev | % reduction Control | stdev |
| 0 | 0.00 | 0.00 | 0.00 | 0 |
| 1 | 44.03 | 28.08 | 26.05 | 16.87 |
| 2 | 55.17 | 17.74 | 44.64 | 38.75 |
| 3 | 60.63 | 15.21 | 41.19 | 34.54 |
| 4 | 61.67 | 14.19 | 36.92 | 20.45 |
| 5 | 63.33 | 13.41 | 38.35 | 16.8 |
| 6 | 71.94 | 8.19 | 41.73 | 16.54 |
| 7 | 72.95 | 9.19 | 36.63 | 16.77 |
| 8 | 76.02 | 11.07 | 41.40 | 14.13 |
| 9 | 81.57 | 11.90 | 37.63 | 12.44 |
| 10 | 84.30 | 11.21 | 37.17 | 15.99 |

The invention is not to be limited in scope by the specific embodiments disclosed in the examples, which are intended as illustrations of a few aspects of the invention, and any embodiments, which are functionally equivalent, are within the scope of this invention. Indeed, various modifications of the invention in addition to those shown and described herein will become apparent to those skilled in the art and are intended to fall within the appended claims.

For any references that have been cited, the entire disclosures of which are incorporated herein by reference.

What is claimed is:

1. A non-aqueous dentifrice composition comprising an effective amount of a bioactive and bio-acceptable glass and a desensitizing effective amount of potassium chloride wherein the bioactive and bio-acceptable glass is calcium sodium phosphosilicate or is a bioactive glass which comprises:
  SiO$_2$ from 40-60 wt. %;
  CaO from 10-30 wt. %;
  Na$_2$O from 10-35 wt. %;
  P$_2$O$_5$ from 2-8 wt. %;
  CaF$_2$ from 0-25 wt. %; and
  B$_2$O$_3$ from 0-10 wt. %;
  wherein the potassium chloride is present in an amount of 2 wt. % to 4 wt. % and the bioactive and biocompatible glass is present in an amount of 1 wt. % to 10 wt. %, each based on the total weight of the composition; and
  the composition further comprises one or more of: (1) one or more fluoride source or (2) one or more sources of silica.

2. The composition of claim 1, wherein the potassium chloride is present in an amount of 2 wt. % to 4 wt. % based on the total weight of the composition.

3. The composition of claim 2, wherein the potassium chloride is present in an amount of 3.75 wt. % based on the total weight of the composition.

4. The composition of claim 1, wherein the composition is incorporated in toothpaste, glycerin gel or mouthwash.

5. The composition of claim 1, further comprising one or more antibacterial agents.

6. The composition of claim 1, further comprising one or more tartar control agents.

7. The composition of claim 1, further comprising one or more thickening agents.

8. The composition of claim 1, wherein the bioactive and biocompatible glass is present in an amount of 3 wt. % to 7 wt. % based on the total weight of the composition.

9. The composition of claim 3, wherein the bioactive and biocompatible glass is present in an amount of 5 wt. % based on the total weight of the composition.

10. The composition of claim 1, further comprising one or more sources of fluoride.

11. The composition of claim 1, further comprising one or more sources of silica.

12. The composition of claim 1, wherein the bioactive and bio-acceptable glass is a bioactive glass which comprises:
  SiO$_2$ from 40-60 wt. %;
  CaO from 10-30 wt. %;
  Na$_2$O from 10-35 wt. %;
  P$_2$O$_5$ from 2-8 wt. %;
  CaF$_2$ from 0-25 wt. %; and
  B$_2$O$_3$ from 0-10 wt. %.

13. The composition of claim 10, wherein the bioactive and bio-acceptable glass is calcium sodium phosphosilicate.

14. A non-aqueous dentifrice composition comprising an effective amount of a bioactive and bio-acceptable glass and a desensitizing effective amount of potassium chloride wherein the bioactive and bio-acceptable glass is calcium sodium phosphosilicate or is a bioactive glass which comprises:
  SiO$_2$ from 40-60 wt. %;
  CaO from 10-30 wt. %;
  Na$_2$O from 10-35 wt. %;
  P$_2$O$_5$ from 2-8 wt. %;
  CaF$_2$ from 0-25 wt. %; and
  B$_2$O$_3$ from 0-10 wt. %;
  wherein the potassium chloride is present in an amount of 2 wt. % to 4 wt. % and the amount of bioactive and biocompatible glass is present in an amount of 3 wt. % to 7 wt. %, each based on the total weight of the composition; and
  the composition further comprises one or more of: (1) one or more fluoride source or (2) one or more sources of silica.

15. A non-aqueous dentifrice composition comprising an effective amount of a bioactive and bio-acceptable glass and a desensitizing effective amount of potassium chloride wherein the bioactive and bio-acceptable glass is calcium sodium phosphosilicate or is a bioactive glass which comprises:
  SiO$_2$ from 40-60 wt. %;
  CaO from 10-30 wt. %;
  Na$_2$O from 10-35 wt. %;
  P$_2$O$_5$ from 2-8 wt. %;
  CaF$_2$ from 0-25 wt. %; and
  B$_2$O$_3$ from 0-10 wt. %;
  wherein the potassium chloride is present in an amount of 3.75 wt. % and the amount of bioactive and biocompatible glass is present in an amount of 5 wt. %, each based on the total weight of the composition; and
  the composition further comprises one or more of: (1) one or more fluoride source or (2) one or more sources of silica.

* * * * *